US008546397B2

(12) United States Patent
Chen et al.

(10) Patent No.: US 8,546,397 B2
(45) Date of Patent: Oct. 1, 2013

(54) DNA METHYLATION INHIBITORS

(75) Inventors: Ching-Shih Chen, Upper Arlington, OH (US); Arthur Y. Shaw, Tucson, AZ (US); Yu-Wei Leu, Chia-Yi (TW); Shu-Huei Hsiao, Chia-Yi (TW)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 13/329,593

(22) Filed: Dec. 19, 2011

(65) Prior Publication Data
US 2012/0157465 A1 Jun. 21, 2012

Related U.S. Application Data

(60) Provisional application No. 61/424,925, filed on Dec. 20, 2010.

(51) Int. Cl.
*A61K 31/497* (2006.01)
(52) U.S. Cl.
USPC .................. 514/252.13; 514/252.12
(58) Field of Classification Search
USPC ....................... 514/252.12, 252.13
See application file for complete search history.

(56) References Cited

U.S. PATENT DOCUMENTS

| 4,938,949 | A | 7/1990 | Borch et al. | |
| 7,981,895 | B2 * | 7/2011 | Watkins et al. | 514/252.12 |
| 2003/0236403 | A1 | 12/2003 | Debernardis et al. | |
| 2007/0032502 | A1 * | 2/2007 | Mallams et al. | 514/252.17 |
| 2008/0269237 | A1 * | 10/2008 | Watkins et al. | 514/252.14 |

FOREIGN PATENT DOCUMENTS

| EP | 674233 | 9/1995 |
| WO | 2006/099193 | 9/2006 |
| WO | 2008/076767 | 6/2008 |

OTHER PUBLICATIONS

Bender et al., "Inhibition of DNA methylation by 5-Aza-2'-deoxycytidine suppresses the growth of human tumor cell lines", Cancer Res., 58 (1), p. 95-101 (1998).
Chen et al., "Synthesis and pharmacological exploitation of clioquinol-derived copper-binding apoptosis inducers triggering reactive oxygen species generation and MAPK pathway activation", Bioorganic & Medicinal Chemistry 17 (20), p. 7239-7249 (2009).
Chuang et al., "Comparison of biological effects of non-nucleoside DNA methylation inhibitors versus 5-aza-2'-deoxycytidine", Mol Cancer Ther, 4, p. 1515-20 (2005).
Greenber et al., "Prostate cancer in a transgenic mouse", Proc Natl Acad Sci USA, 92 pp. 3439-3443 (1995).
Hewagama et al., "The genetics and epigenetics of autoimmune diseases", J Autoimmun 33 (1), pp. 3-11 (2009).
Hsiao et al., "Excavating relics of DNA methylation changes during the development of neoplasia", Semin Cancer Biol. 19, p. 198-208 (2009).
Hsiao et al. "DNA methylation of the Trip10 promoter accelerates mesenchymal stem cell lineage determination", Biochem Biophys Res Commun 400 (3), p. 305-12 (2010).

(Continued)

*Primary Examiner* — My-Chau T Tran
(74) *Attorney, Agent, or Firm* — Tarolli, Sundheim, Covell & Tummino LLP

(57) ABSTRACT

A number of DNA methylation inhibitors are described. The DNA methylation inhibitors were identified using a two-component enhanced green fluorescent protein reporter system to screen a compound library containing procainamide derivatives. The DNA methylation inhibitors can be used for cancer therapy and prevention.

6 Claims, 4 Drawing Sheets

(56) References Cited

OTHER PUBLICATIONS

Hsu et al., "Targeted methylation of CMV and E1A viral promoters", Biochem Biophys Res Commun, 402 (2), p. 228-34 (2010).

Konieczny et al., "5-Azacytidine induction of stable mesodermal stem cell lineages from 10T1/2 cells: evidence for regulatory genes controlling determination", Cell 38 (3), pp. 791-800 (1984).

Lee et al. "Procainamide is a specific inhibitor of DNA methyltransferease 1", J Biol Chem 280, p. 40749-56 (2005).

Lin et al., "Reversal of GSTP1 CpG Island hypermethylation and reactivation of π-class gluthathione S-transferase (GSTP1) expression in human prostate cancer cells by treatmenet with procainamide", Cancer Res. 61, p. 8611-6 (2001).

Lin et al., "Identification of novel DNA methylation inhibitors via a two-component reporter gene system", J of Biomedical Science, 18: 3, pp. 1-8 (2011).

Lu et al., "Demethylation of the same promoter sequence increases CD70 expression in lupus T cells and T cells treated with lupus-inducing Drugs", J. Immunol. 175, p. 6212-9 (2005).

Martelli et al., "Testing of metoclopramide and procainamide for their ability to induce genotoxic effects in cultured mammalian cells", Toxicol. Appl. Pharmacol 131, p. 185-91 (1995).

Mereto et al., "Evaulation of DNA-damaging, clastogenic, and promoting activities of metoclopramide and procainamide in rats", Toxicol Appl Pharmacol 131(2), p. 192-7 (1995).

Michalowsky et al., "Gene structure and transcription in mouse cells with extensively demethylated DNA", Mol Cell Biol 9 (3), pp. 885-892 (1989).

Polin et al., "Treatment of human prostate tumors PC-3 and TSU-PR1 with standard and investigational agents in SCID mice", Invest New Drugs 15: pp. 99-108 (1997).

Sauntharajah et al., "Effects of 5-aza-2'deoxycytidine on fetal hemoglobin levels, red cell adhesion, and hematopoietic differentiation in patients with sickle cell disease", Blood 102 (12), pp. 3865-3870 (2003).

Segura-Pacheco et al. "Reactivation of tumor suppressor genes by the cardiovascular drugs hydralazine and procainamide and their potential use in cancer therapy", Clin Cancer Res, 9, pp. 1596-1603 (2003).

Shaw et al., "Pharmacological exploitation of the a1-Adrenoreceptor antagonist doxazosin to develop a novel class of antitumor agents that block intracellular protein kinase B/AKT activation", J of Medicinal Chemistry 47 (18), p. 4453-4462 (2004).

Shaw et al., "synthesis of 2-styrylchromones as a novel class of antiproliferative agents targeting carcinoma cells", European J of Medicinal chemistry, 44 (6), p. 2552-2562 (2009).

Shaw et al., "Microwave-assisted base-catalyzed cyclization and nucleophilic substitution of O-azidobenzanilides to synthesize 1,2-Disubstituted Indazol-3-ones", Synthetic Communications 39 (15), p. 2647-2663 (2009).

Shaw et al., "Synthesis and structure-activity relationship study of 8-hydroxyquinoline-derived Mannich bases as anticancer agents", European J of Medicinal Chemistry 45 (7), p. 2860-2867 (2010).

Villar-Garea et al., "Procaine is a DNA-demethylating agent with growth-inhibitory effects in human cancer cells", Cancer Res 63, p. 4984-9 (2003).

Yan et al., "Applications of CpG island microarrays for high-throughput analysis of Dna methylation", J Nutr 132 (8 Suppl) p. 2430S-2434S (2002).

Yoo, et al., "Epigenetic therapy of cancer: past, present and future", Nat Rev Drug Discov, 5 (1), p. 37-50 (2006).

International Search Report from PCT/US11/65754 dated Jul. 18, 2012.

PubChemCompound, datasheet (online compound summary), retrieved from http://pubchem.ncbi.nlm.nih.gov/search/search.cgi>, see CID 704295, CID 712924, CID 746514, CID 797560, CID 801806, CID 80699E, CID 808712, CID 1071339, CID 1078364, CID 1133956, Aug. 23, 2012.

Teles et al., "Benzopyrans from Curvularia sp., an endophytic fungus associated with Ocotea corymbosa (Lauraceae)". Phytochemistry, vol. 66, No. 19, pp. 2363-2367 (2005).

Momoi, et al., "Cytotoxic activity of styrylchromones against human tumor cell lines", In Vivo, vol. 19, No. 1, pp. 157-163 (2005).

* cited by examiner

DNA METHYLATION INHIBITORS

CONTINUING APPLICATION DATA

This application claims the benefit of U.S. Provisional Application Ser. No. 61/424,925, filed Dec. 20, 2010, the disclosure of which is incorporated by reference herein.

GOVERNMENT FUNDING

The present invention was supported by Grant R01 CA112250 from the National Cancer Institute of the National Institutes of Health. The Government has certain rights in this invention.

BACKGROUND

DNA methylation-mediated silencing of genes has been implicated in the pathogenesis of many diseases including cancer. Hsiao et al., Semin Cancer Biol, 19 p. 198-208 (2009). Since the discovery that DNA methylation-mediated gene silencing is a reversible event, identifying small-molecule DNA methylation inhibitors, either natural or synthetic, for cancer treatment has been the focus of significant investigation. Yoo, C. B. and P. A. Jones, Nat Rev Drug Discov, 5(1), p. 37-50 (2006). Among many agents with DNA methylation-modifying capability, 5-aza-2'-deoxycytidine (decitabine; 5-Aza) is the best-known DNA demethylation agent. 5-Aza exerts its effect by inhibiting DNA methyltransferases (DNMTs), the key enzymes responsible for initiating or maintaining the DNA methylation status, thereby facilitating the re-expression of tumor suppressor genes through DNA hypomethylation. Its therapeutic efficacy is manifest by the Food and Drug Administration approval for the treatment of myelodysplastic syndromes. While 5-Aza is a potent DNA demethylation agent, its use is associated with increased incidences of bone marrow suppression, including neutropenia and thrombocytopenia, due to the disruption of DNA synthesis. Chuang et al., Mol Cancer Ther, 4, p. 1515-20 (2005). In addition, shorter half-life hinders the effective delivery of 5-Aza to the tumor site.

Recently, procainamide has emerged as a potential DNA demethylating agent for clinical translation. Evidence indicates that procainamide inhibits DNMT1 by reducing the affinity with its two substrates: hemimethylated DNA and S-adenosylmethionine. Lee et al., J. Biol Chem, 280, p. 40749-56 (2005); Lin et al., Cancer Res. 61, p. 8611-6 (2001); Lu et al., J. Immunol. 174, p. 6212-9 (2005). Through DNA demethylation, procainamide causes growth arrest (Villar-Garea et al., Cancer Res. 63, p. 4984-9 (2003)) and reactivation of tumor suppressor genes in cancer cells. Segura-Pacheco et al., Clin Cancer Res, 9, p. 1596-603 (2003). Moreover, as an anti-arrhythmic drug, procainamide has a well-characterized safety profile without side effects commonly associated with nucleoside analogues. Martelli et al., Toxicol. Appl. Pharmacol. 131, p. 185-91 (1995); Mereto et al., Toxicol Appl Pharmacol. 131(2), p. 192-7 (1995). However, in contrast to 5-Aza, procainamide requires high concentrations ($\geq 50$ µM) to be effective in DNA demethylation in suppressing cancer cell growth. Lee et al., J. Biol. Chem. 280, p. 40749-56 (2005). Accordingly, there remains a need for additional DNA methylation inhibitors, particularly those with greater potency or lower cytotoxicity.

SUMMARY OF THE INVENTION

The inventors have embarked on the pharmacological exploitation of procainamide to identify novel DNA demethylating agents using their two-component enhanced green fluorescent protein reporter gene system. A number of the compounds identified showed low cytotoxicity and significant activity as DNA methylation inhibitors.

Based on the testing, 46 derivatives showed significant inhibition of DNA methylation, of which 36 did not cause apparent cell death. These 36 compounds belonged to three structural series, represented herein by formulas I, II, and III.

DNA methylation inhibitors can be used for a variety of different purposes. DNA methylation inhibitors can be used for cancer treatment, and can also be used to control stem cell differentiation and treat diseases like sickle cell disease. The compounds of the present invention can be placed in contact with a cell to provide inhibition of DNA methylation, and can be administered to a subject in a pharmaceutical composition to treat or prevent cancer.

DETAILED DESCRIPTION OF THE INVENTION

Figure 1:
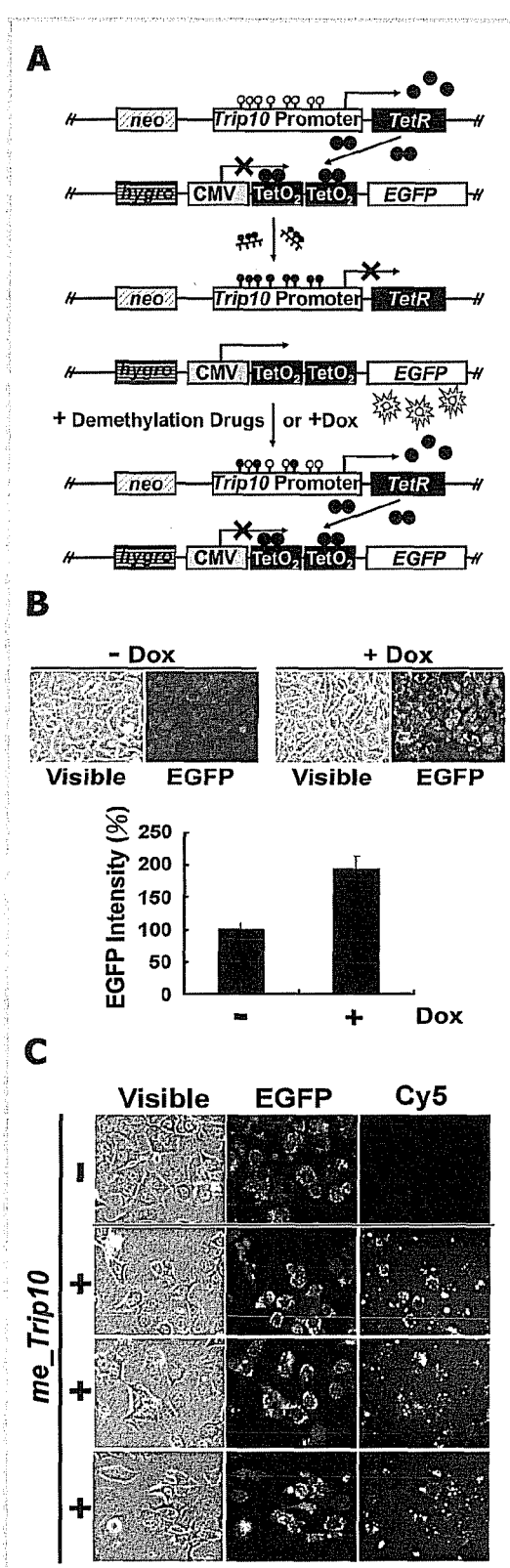
FIG. 1 provides schemes of the reporter gene system and results obtained using in the screening system for demethylation agents. Section (A) provides a schematic depiction of the reporter system in MCF7 cells. The reporter gene system consists of two constructs (top). Expression of Tet repressor (TetR) was under the regulation of Trip10 promoter. The addition of doxycycline (Dox) or targeted methylation of Trip10 promoter (center) blocks the silencing/binding of Tet repressor onto the Tet operator (TetO$_2$) thus the EGFP would express and become detectable with fluorescence microscope. Bottom, demethylation of the Trip10 promoter restores the expression of Tet repressor and thus silences the EGFP. Open circles: unmethylated CpG dinucleotides; filled circles: methylated CpG dinucleotides. Section (B) provides results demonstrating the validation of the reporter gene system. As shown, the presence of doxycycline did not affect the cell density, but increased the intensity of EGFP substantially (top). Histograms show the quantified EGFP intensity in the presence or absence of doxycycline (bottom). The EGFP intensity was analyzed and quantified by Image J. Section (C) shows the tracking of the transfected me_Trip10 DNAs. In vitro methylated Trip10 promoter DNAs were labelled with or without (control) Cy5 and then used to transfect the MCF7 cells. There is a high degree of overlap between the EGFP-expressing cells and Cy5-positive cells, suggesting the high transfection efficiency in this system.

The present invention provides a number of DNA methylation inhibitors. The DNA methylation inhibitors were identified using a two-component enhanced green fluorescent protein reporter system to screen a compound library containing procainamide derivatives.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anti-cancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alkyl groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclobutyl, cyclobutylmethyl, cyclopentyl, and cyclohexyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo can also be used alone to indicate an attached halogen atom. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. This is true regardless of whether or not the enantiomers are shown in chemical formula representing the compounds. For example, if a compound that includes a chiral center is shown without any indication of stereochemistry, it is presumed to represent all possible stereoisomers of the compound. It should be understood that the term "compound" includes any or all of such forms, whether explicitly stated or not (although at times, "salts" are explicitly stated).

Treat", "treating", and "treatment", etc., as used herein, refer to any action providing a benefit to a subject afflicted with a condition or disease such as cancer. Treatment can result in complete remission of the cancer, but can also include lesser effects, including improvement in the condition through lessening or suppression of at least one symptom, delay in progression of the disease, avoiding the development of additional symptoms in one known to be afflicted with cancer, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

One aspect of the invention provides a number of compounds that have been prepared as procainamide derivatives. In one embodiment, a number of compounds based on formulas I were prepared:

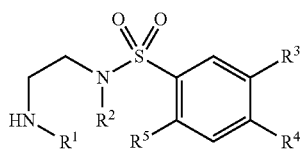

I wherein $R^1$ and $R^2$ are either both hydrogen or are linked $CH_2$ moieties forming an unsubstituted ethylene group, and wherein $R^3$, $R^4$, and $R^5$ are independently selected from the group consisting of H, halo, $C_1$-$C_4$ alkyl, $NO_2$, OH, OMe, $CF_3$, and $OCF_3$ moieties. These include the compounds of the "IM" series in the compound library, including compounds IM-1, IM-2, IM6, IM7, IM8, IM9, IM11, IM12, IM14, IM15, IM18, IM19, IM24, IM25, and IM32.

In another embodiment, $R^1$ and $R^2$ are linked $CH_2$ moieties forming an unsubstituted ethylene group, thereby forming a piperazine ring, and $R^5$ is H. In yet another embodiment, $R^1$ and $R^2$ are linked $CH_2$ moieties forming an unsubstituted ethylene group and $R^3$ is H.

In a further embodiment, the compounds of formula I have the structure:

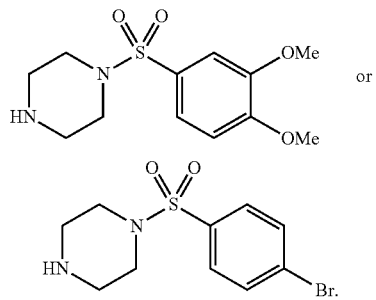

In another embodiment, a number of compounds based on formulas II (i.e., formula IIa and formula IIb) were prepared:

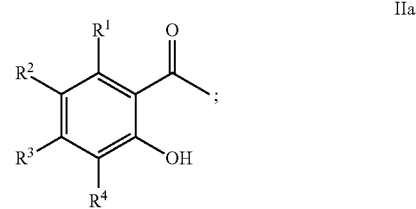

IIa

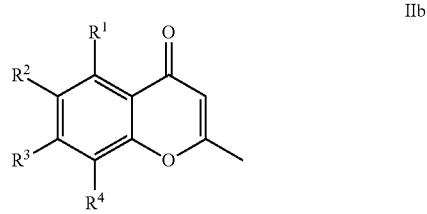

IIb wherein $R^1$, $R^2$, $R^3$, and $R^4$ are independently selected from H, OH, and OMe. These include the compounds of the "CI" series in the compound library, including compounds CI-1-1, CI-1-2, CI-1-3, CI-3-2, CI-4-1, CI-4-2, CI-5-1, CI-5-2, CI-6-1, and CI-6-2.

In another embodiment, the compound is only according to formula IIa. In yet further embodiments, the compounds of formula II are defined such that $R^1$, $R^2$, $R^3$, and $R^4$ are independently selected from H and OMe, and at least one of $R^1$, $R^2$, $R^3$, and $R^4$ is OMe.

In a further embodiment, the compounds of formula IIa have the structure:

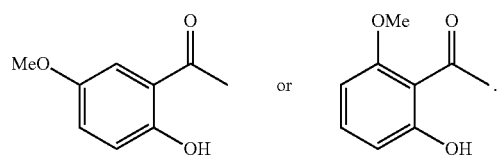

In another embodiment, a number of compounds based on formulas III were prepared:

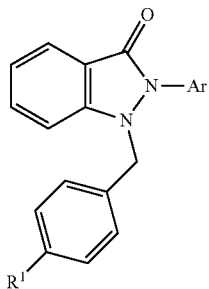

Figure 2:
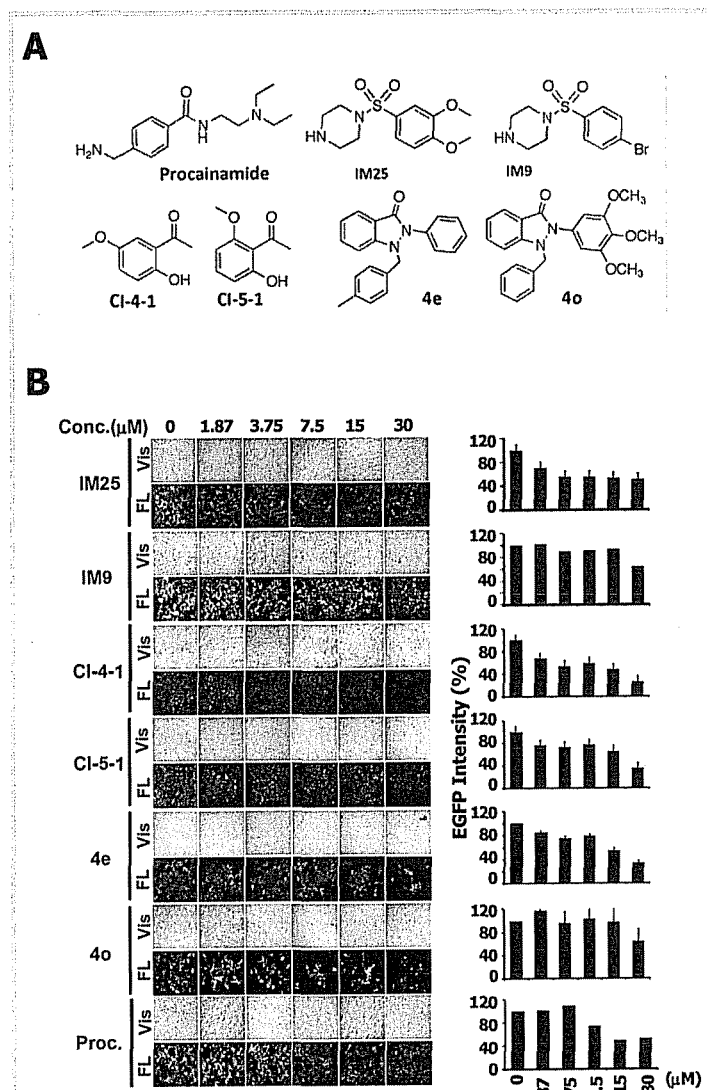
FIG. 2 provides chemical structures and results obtained for the identification of active DNA demethylating agents. Section (A) shows the chemical structures of procainamide, the three selected agents IM25, CI-4-1, and 4e and their structurally related analogues IM9, CI-5-1, and 4o. Section (B) shows the potencies of procainamide, IM25, IM9, C-4-1, CI-5-1, 4-e, and 4o in attenuating EGFP expression in the two-component reporter system. The EGFP intensities in individual treatments are illustrated on the right.

III wherein $R^1$ is selected from the group consisting of H, halo, $C_1$-$C_4$ alkyl, $NO_2$, OH, OMe, $CF_3$, and $OCF_3$ moieties and Ar is a substituted or unsubstituted phenyl or pyridyl group, wherein the one or more optional substituents are chosen from the group consisting of H, halo, $C_1$-$C_4$ alkyl, $NO_2$, OH, OMe, $CF_3$, and $OCF_3$ moieties. These include the compounds of the "4" series in the compound library, including compounds 4b, 4c, 4d, 4e (shown in FIG. 2), 4f, 4g, 4i, 4k, 4n, and 4o.

In further embodiments of the compound of formula III, $R^1$ is H. In yet further embodiments, Ar is an unsubstituted phenyl group.

In a further embodiment, the compounds of formula III have the structure:

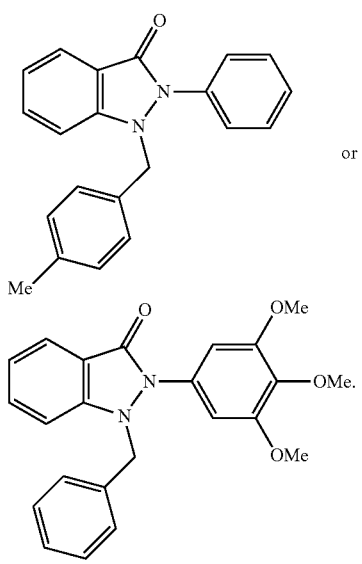

Cancer Treatment Using the Compounds of the Invention

The present invention provides methods for treating or preventing cancer in a subject that includes administering to the subject a pharmaceutical composition including a compound according to formula I, II, or III or a pharmaceutically acceptable salt thereof. Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, hepatic cancer, non-small cell lung cancer, colon cancer, central nervous system cancer, melanoma, ovarian cancer, renal cancer, prostate cancer, and breast cancer. Preferred types of cancer include those resulting in solid tumors such as breast cancer, prostate cancer, lung cancer, and colon cancer.

Accordingly, in another aspect, the invention provides a method for treating or preventing cancer in a subject, that includes administering to the subject a pharmaceutical composition including a compound of formula I or a pharmaceutically acceptable salt thereof:

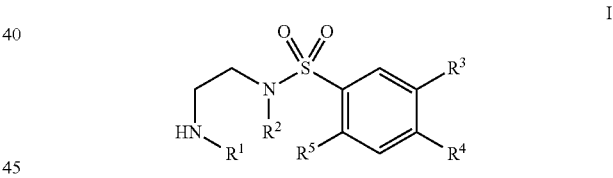

I wherein $R^1$ and $R^2$ are either both hydrogen or are linked $CH_2$ moieties forming an unsubstituted ethylene group, and wherein $R^3$, $R^4$, and $R^5$ are independently selected from the group consisting of H, halo, $C_1$-$C_4$ alkyl, $NO_2$, OH, OMe, $CF_3$, and $OCF_3$ moieties.

In another aspect, the invention provides a method for treating or preventing cancer in a subject, that includes administering to the subject a pharmaceutical composition including a compound of formula IIa or IIb or a pharmaceutically acceptable salt thereof:

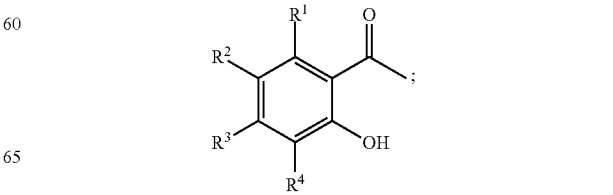

IIa

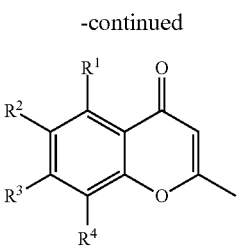

wherein $R^1$, $R^2$, $R^3$, and $R^4$ are independently selected from H, OH, and OMe.

In another aspect, the invention provides a method for treating or preventing cancer in a subject, that includes administering to the subject a pharmaceutical composition including a compound of formula III or a pharmaceutically acceptable salt thereof:

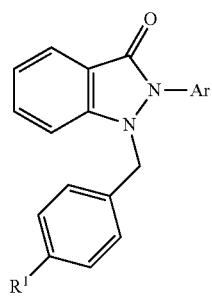

wherein $R^1$ is selected from the group consisting of H, halo, $C_1$-$C_4$ alkyl, $NO_2$, OH, OMe, $CF_3$, and $OCF_3$ moieties and Ar is a substituted or unsubstituted phenyl or pyridyl group, wherein the one or more optional substituents are chosen from the group consisting of H, halo, $C_1$-$C_4$ alkyl, $NO_2$, OH, OMe, $CF_3$, and $OCF_3$ moieties.

While not intending to be bound by theory, it is thought that the DNA methylation inhibitors of the present invention treat or prevent cancer when administered to a subject by reversing or preventing epigenetic alteration and the resulting transcriptional silencing of important genes involved in cancer such as tumor suppressor genes (e.g., caretaker and gatekeeper genes). Epigenetic alterations are found in nearly all types of cancer, and involve methylation of the DNA sequence, rather than changes to the sequence itself. The most studied faun of epigenetic alteration is CpG dinucleotide methylation. As shown in Example I herein, compounds of formulas I, II, and III showed the ability to decrease methylation of the CpG-rich Trip10 promoter used in the EGFP reporter gene system.

DNA methyltransferases (e.g., DNA methyltransferase 1; DNMT1) are enzymes involved in methylating DNA in cells. The DNA methylation inhibitors of the present invention inhibit DNMT1, resulting in a reactivation of tumor suppressor genes in cancer cells, leading to the death or cytostasis of these cancer cells.

The compounds of the invention can be used to provide prophylactic and/or therapeutic treatment. The compounds of the invention can, for example, be administered prophylactically to a subject in advance of the occurrence of cancer. Prophylactic (i.e., preventive) administration is effective to decrease the likelihood of the subsequent occurrence of cancer in the subject, or decrease the severity of cancer that subsequently occurs. Prophylactic treatment may be provided to a subject that is elevated risk of developing cancer, such as a subject with a family history of cancer or exposure to high levels of carcinogens.

DNA methylation inhibitors of the present invention can also be used to treat a variety of diseases other than cancer. Examples of other diseases involving aberrant DNA methylation include autoimmune diseases (Hewagama et al., J. Autoimmun 33(1), 3-11 (2009)) and sickle cell disease (Sauntharajah et al., Blood, 102(12), 3865-70 (2003)). Compounds of the present invention can also be used to affect DNA methylation outside of the context of disease treatment. For example, DNA methylation inhibitors can be used to alter gene expression and control stem cell differentiation. See Michalowsky et al., Mol. Cell. Biol. 9(3), 885-92 (1989) and Konieczny et al., Cell, 38(3), 791-800 (1984).

The compounds of the invention can also be administered therapeutically to a subject that is already afflicted by cancer. In one embodiment of therapeutic administration, administration of the compounds is effective to eliminate the cancer; in another embodiment, administration of the compounds is effective to decrease the severity of the cancer or lengthen the lifespan of the subject so afflicted. The subject is preferably a mammal, such as a domesticated farm animal (e.g., cow, horse, pig) or pet (e.g., dog, cat). More preferably, the subject is a human.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Candidate agents can also be evaluated by directly testing their effectiveness as DNA methylation inhibitors. A suitable method for doing this is the two-component enhanced green fluorescent protein (EGFP) reporter gene system described further herein.

Another aspect of the invention provides a method of inhibiting DNA methylation in a cell by contacting the cell with a compound according to formula I, II, or III, or a pharmaceutically acceptable salt thereof. As described herein, the compounds of the present invention have the ability to inhibit DNA methylation by DNA methyltransferases. For example, the compounds of the invention can inhibit DNA methylation as a result of inhibiting the activity of DNA methyltransferase 1. Inhibition of the DNA methyltransferase occurs upon contact by the DNA methylation inhibitor.

The method involves contacting the cell with one of the compounds of the present invention. The cell can be contacted by the compound either in vivo or ex vivo. The cell can be an animal cell, such as a mammalian or human cells. The cell can be a healthy cell or it can be a diseased cell such as a cancer cell. The cell can be contacted by the compound as a result of the compound be added to the environment of the cell. The environment can be an artificial environment such as a tissue culture environment, or the cell can be in a natural environment such as being present within an animal. The compound contacts the cell by diffusion within the environment, and will be taken up or diffuse through the cell to contact DNA methyltransferase and thereby provide the beneficial effects described herein. The compound can be delivered by itself or in a pharmaceutical composition. Use of a pharmaceutical composition and methods of administration known to those skilled in the art is particularly useful for contacting a cell within a natural environment such as a subject.

Administration and Formulation of the Compounds of the Invention

The present invention also provides pharmaceutical compositions that include compounds such as those defined by the formulae described herein as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compounds of the invention, or by separately reacting a purified compound of the invention with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds of the invention together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound of the invention (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

Methods for the preparation of a number of the compounds of the invention are available. For example, a number of papers have been published on preparing compounds according to formula I. See Shaw et al., Journal of Medicinal Chemistry 47(18), 4453-4462 (2004); Shaw et al., European Journal of Medicinal Chemistry, 45(7), 2860-2867 (2010); Chen et al., Bioorganic & Medicinal Chemistry, 17(20), 7239-7247 (2009). The preparation of compounds according to formula II can be assisted by Shaw et al., European Journal of Medicinal Chemistry, 44(6), 2552-2562 (2009). Finally, the preparation of compounds according to formula III can be assisted by Shaw et al., Synthetic Communications, 39(15), 2647-2663 (2009).

The present invention is illustrated by the following examples. It is to be understood that the particular examples, materials, amounts, and procedures are to be interpreted broadly in accordance with the scope and spirit of the invention as set forth herein.

EXAMPLES

Example 1

Monitoring DNA Methylation Status Using a Two-Component EGFP Reporter Gene System The inventors have reported a two-component enhanced green fluorescent protein (EGFP) reporter gene system for the visualization and quantization of dynamic changes in targeted DNA methylation in bone marrow-derived mesenchymal stem cells or cancer cell lines. Hsiao et al., Biochem Biophys Res Commun, 400(3), p. 305-12 (2010); Hsu et al., Biochem Biophys Res Commun, 402(2), p. 228-34 (2010). This system gives a direct and concomitant measurement and evaluation of DNA demethylation and cytotoxicity in living cells, thus providing an expedient screening platform for identifying demethylating agents.

Methods

Cell culture and drug treatment. MCF7 breast cancer cells, obtained from American Type Culture Collection, were grown in Minimal Essential Medium (MEM; Invitrogen), supplemented with 10% FBS, 2 mM L-glutamine, and 100 µg/ml penicillin/streptomycin. Cells were cultured at 37° C. in a humidified incubator containing 5% $CO_2$. Medium changes were performed twice weekly and cell passages were performed at 90% confluence. To maintain the two-component constructs in MCF7 cells, 200 µg/mL of hygromycin B (Invitrogen) and 500 µg/mL of Geneticin (G418, Calbiochem) were included in culture medium. 5-Aza and procainamide were purchased from Sigma-Aldrich. Compounds being tested were dissolved in DMSO as stock solutions, and added to culture medium with final DMSO concentrations of 0.3% and 1.2% (v/v) for 7.5 µM and 30 µM of testing drugs, respectively. Control cells received DMSO vehicle. During the 5-day treatment period, medium was changed on the third day of treatment along with the addition of 17β-estradiol (E2, 10 ng/ml).

In vitro DNA methylation. PCR-amplified and purified Trip10 promoter (4 µg) was incubated with 20 U of CpG methyltransferase (SssI, New England BioLabs) at 37° C. for 4 h in the presence of 160 µM S-adenosylmethionine to induce methylation at the Trip10 promoter DNA. Complete conversion was indicated by the resistance of methylated Trip10 DNA to methylation-sensitive restriction enzymes (HpaII, New England BioLabs).

Transfection. In vitro methylated Trip/0 promoter DNAs (0.4 µg) were denatured and used to transfect $1 \times 10^5$ cells/well in 6-well plate at day 1, 3, and 5 using DMRIE-C (Invitrogen) according to the manufacturer's instruction. Unmethylated PCR products were transfected as mock controls. Tracking of the transfected DNAs was performed by using the LabelIT Tracker Cy5 Intracellular Nucleic Acid Localization Kit (Minus) by following the manufacture's instruction. Cells were monitored by fluorescence microscopy (Axiovert 200M, ZEISS) and analyzed with the MetaMorph software.

Bisulfite conversion. Genomic DNA (0.5 µg) was bisulfite-converted by the EZ DNA Methylation Kit (Zymo) by following the manufacturer's instructions.

qMSP. Bisulfite converted DNAs were PCR-amplified by using appropriate PCR primers. Universal methylated DNAs (Millipore) were used as positive control. Col2A1 was used as a loading control and to amplify the serial diluted (1/10, 1/100 and 1/1000) bisulfite-converted universal methylated DNAs to generate the standard curve for quantization in real time PCR machine (Bio-Rad, iQ5). The methylation percentage was calculated as [(Intensity of Amplifications by Trip10 MSP primer set)×100]/(Intensity of Amplifications by Col2A1 MSP primer set) (%). The qMSP was performed in a 25 µL, of reaction mixture containing 4 µL of template (bisulfate treated DNA), 2 µL of primer pair (2.5 µM), 12.5 µL of 2× reaction buffer (SYBR Green real time PCR Master Mix, Toyobo), and 6.5 µL of $H_2O$.

Analysis of EGFP expression was performed by fluorescence microscopy (Axiovert 200M, ZEISS) with the MetaMorph software. Images and intensities of EGFP of more than 600 cells were analyzed by the image analysis program NIH Image (Image J).

Western blotting. Equal amounts of protein in cell lysates were separated in 10% SDS polyacrylamide gels and then transblotted to nitrocellulose membranes. After blocking with non-fat milk, the membrane was washed and incubated with antibodies against GFP (Abeam) or (β-actin (Sigma-Aldrich). The membrane was washed, and then incubated with anti-rabbit immunoglobulin G-horseradish peroxidase. After final wash, the proteins were visualized by enhanced chemiluminescence. Immunoblotting data were analyzed by NIH Image.

Cell viability assay. Cell viability was assessed using MTT [3-(4,5-dimethylthiazol-2-yl)-2,5-diphenyl-2H-tetrazolium bromide, Sigma-Aldrich) in six replicates. MCF7 cells were seeded at 4,000 cells per well in 96-well plates, and treated with test agents at different concentrations. After 5-day treatment, cells were incubated in medium containing 0.5 mg/ml MTT at 37 C for 4 h. Reduced MTT was solubilized in 200 µl/well of DMSO for determination of absorbance of 595 nm using a microplate reader.

ELISA. Enzyme-linked immunosorbent assay (ELISA) was performed using the GFP ELISA kit (Cell Biolabs, San Diego, Calif.) according to the manufacture's instruction.

Differential Methylation Hybridization (DMH) Array. DMH was performed according to a reported procedure. Yan et al., J Nutr, 132(8 Suppl): p. 2430S-2434S (2002). Amplicons prepared from control (vehicle-treated) MCF7 cells were labeled with Cy5 and the amplicons prepared from drug-treated cells were labeled with Cy3. Labeled DNAs were co-hybridized onto 244K Agilent promoter array. Array hybridization results were normalized with LOWESS and a cutoff of 4 folds was used.

Statistics. ELISA and MTT results were analyzed by F-test. Significant demethylated loci were confirmed by ANOVA from DMH results. Linear regression was used to deduce the global methylation states before and after the demethylation agent treatment.

Results

Monitoring DNA methylation status by a two-component EGFP reporter gene system. The inventors have described the development of a two-component EGFP reporter gene system to confirm the level of transcriptional silencing and to visualize DNA methylation of the Trip 10 promoter in the differentiation of bone marrow-derived mesenchymal stem cells. Hsiao et al., Biochem Biophys Res Commun, 400(3), p. 305-12 (2010) As illustrated in FIG. 1A, the system consists of two constructs. The first construct consists of the CpG-rich Trip10 promoter region, which governs the expression of downstream Tet repressor. The Trip10 promoter also contains an estrogen receptor (ER)-binding site, which is essential for the gene expression in ER-positive MCF7 breast cancer cells. The second construct contains two Tet repressor-binding sites, Tet operator (TetO$_2$), which is located between the viral CMV promoter and the EGFP reporter gene. When the Trip10 promoter in the first construct was un-methylated, the expressed Tet repressor would block the EGFP expression by binding to the TetO$_2$. Conversely, methylation of Trip10 promoter would suppress the expression of Tet repressor and thus de-repress the EGFP expression. These two constructs were co-transfected into MCF7 cells, and transfectants containing both constructs were selected by hygromycin and G418 and confirmed by PCR. To validate the co-transfection and the two-component regulation, doxycycline (Dox) was added to interfere with the expressed Tet repressor and de-repress the EGFP expression (FIG. 1B). To examine the transfection efficiency, the in vitro methylated Trip10 (me_Trip10) DNAs were coupled with Cy5 and then transfected into the MCF7 cells. The data indicate a strong correlation between Cy5-expression and EGFP expression in these cells (FIG. 1C), suggesting high transfection efficiency.

The inventors have validated this two-component EGFP reporter gene system by exposing the transfected MCF7 cells to different concentrations of 5-Aza and procainamide. After 5-day treatment, both agents showed dose-dependent, repressive effects on EGFP expression levels relative to DMSO control, as visualized by fluorescence microscopy, with relative potency of 5-Aza greater than procainamide (FIG. 2B). Equally important, as these two drugs did not cause morphological changes [light microscopy (Vis)] or suppression of cell viability (FIG. 3A), these findings indicate that this reduction in EGFP expression was not caused by drug-induced cell death, suggesting a direct consequence of DNA demethylation.

Example 2

Screening of a Compound Library Using the Two-component Reporter System

The inventors applied the DNA methylation-targeted reporter system for the screening of a compound library to identify novel DNA methylation inhibitors. As the exact mode of action of procainamide in decreasing the binding DNMT1 with its substrate remains undefined, the inventors used procainamide as a scaffold to develop a focused compound library, together with a number of other readily available compounds for screening via this two-component system.

Screening of a compound library using the two-component reporter system. After validating the reporter system, the inventors assessed the abilities of individual compounds in the compound library, each at 7.5 µM, to mediate DNA demethylation. This library consists of 169 compounds, the majority of which were procainamide derivatives, as shown in Table 1:

TABLE I

Chemical structures of the individual compounds of the compound library used for screening

| Cp | Structure |
|---|---|
| SC-4m-2 | 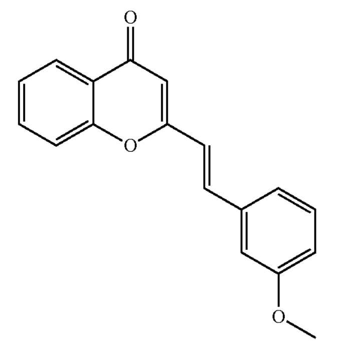 [SMILES: COc1cccc(/C=C/c2cc(=O)c3ccccc3o2)c1] |
| SC-4m-3 | 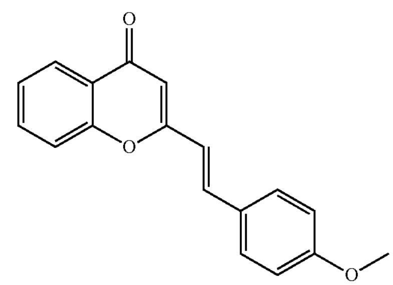 [SMILES: COc1ccc(/C=C/c2cc(=O)c3ccccc3o2)cc1] |
| SC-4m-4 | 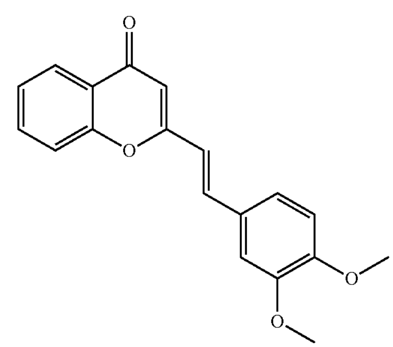 [SMILES: COc1ccc(/C=C/c2cc(=O)c3ccccc3o2)cc1OC] |
| SC-4m-5 | 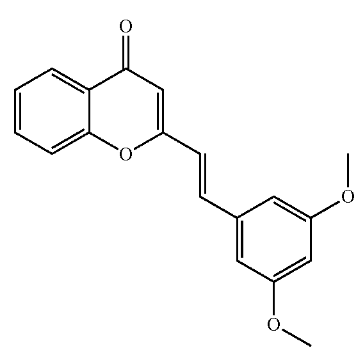 [SMILES: COc1cc(/C=C/c2cc(=O)c3ccccc3o2)cc(OC)c1] |

TABLE I-continued
Chemical structures of the individual compounds of the compound library used for screening
| Cp | Structure |
|---|---|
| SC-4m-6 | 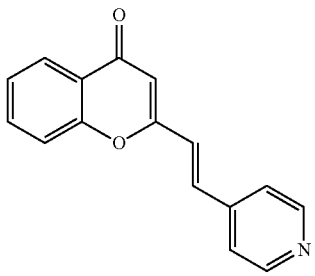 [SMILES: O=c1cc(/C=C/c2ccncc2)oc2ccccc12] |
| SC-4m-7 | 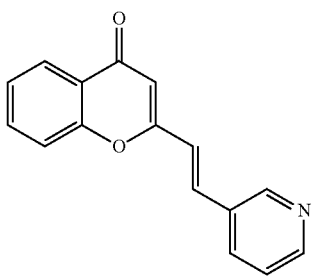 [SMILES: O=c1cc(/C=C/c2cccnc2)oc2ccccc12] |
| SC-4m-8 | 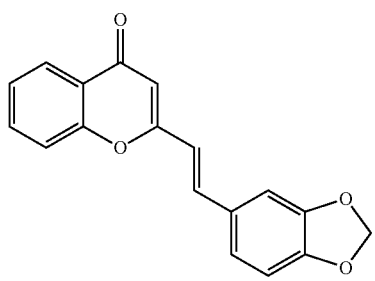 [SMILES: O=c1cc(/C=C/c2ccc3c(c2)OCO3)oc2ccccc12] |
| PMB-KAI-2 | 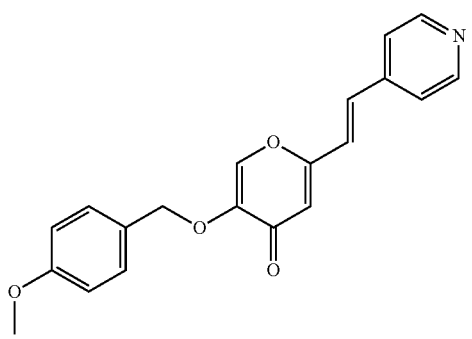 [SMILES: COc1ccc(COc2coc(/C=C/c3ccncc3)cc2=O)cc1] |
| KAI-1 | 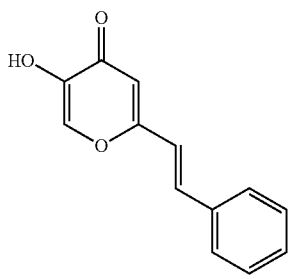 [SMILES: O=c1cc(/C=C/c2ccccc2)occ1O] |
TABLE I-continued
Chemical structures of the individual compounds of the compound library used for screening
| Cp | Structure |
|---|---|
| SC-4a | 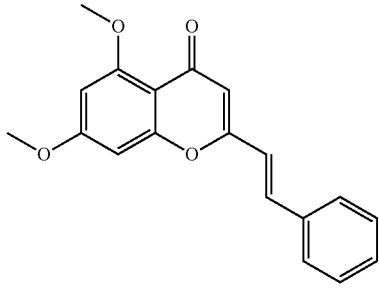 [SMILES: COc1cc(OC)c2c(=O)cc(/C=C/c3ccccc3)oc2c1] |
| SC-4b | 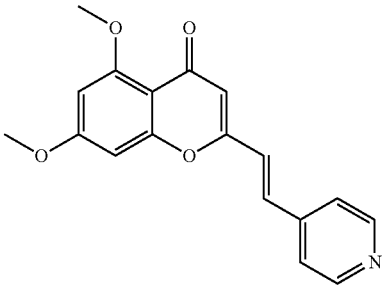 [SMILES: COc1cc(OC)c2c(=O)cc(/C=C/c3ccncc3)oc2c1] |
| SC-4c | 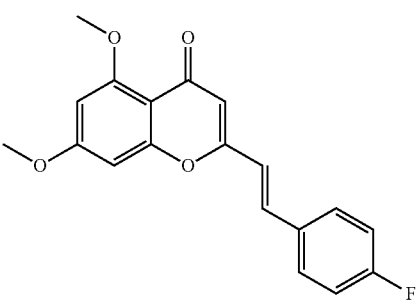 [SMILES: COc1cc(OC)c2c(=O)cc(/C=C/c3ccc(F)cc3)oc2c1] |
| SC-4d | 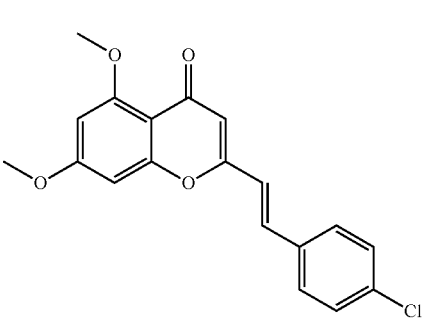 [SMILES: COc1cc(OC)c2c(=O)cc(/C=C/c3ccc(Cl)cc3)oc2c1] |
| SC-4e | 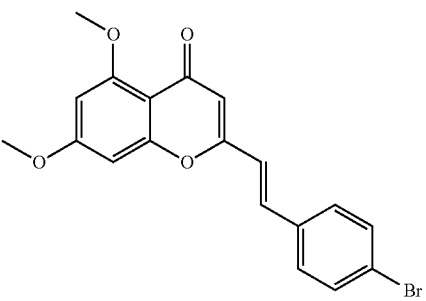 [SMILES: COc1cc(OC)c2c(=O)cc(/C=C/c3ccc(Br)cc3)oc2c1] |

TABLE I-continued

Chemical structures of the individual compounds of the compound library used for screening

| Cp | Structure |
|---|---|
| SC-4f | (5,7-dimethoxy-2-(4-methoxystyryl)-4H-chromen-4-one) |
| M1 | (2-((4-(phenylsulfonyl)piperazin-1-yl)methyl)phenol) |
| M2 | (2-((4-(phenylsulfonyl)piperazin-1-yl)methyl)pyridin-3-ol) |
| M5 | (2-((4-(phenylsulfonyl)piperazin-1-yl)methyl)naphthalen-1-ol) |
| M6 | (7-((4-(phenylsulfonyl)piperazin-1-yl)methyl)quinolin-8-ol) |
| M7 | (7-((4-((4-fluorophenyl)sulfonyl)piperazin-1-yl)methyl)quinolin-8-ol) |
| M8 | (7-((4-((4-chlorophenyl)sulfonyl)piperazin-1-yl)methyl)quinolin-8-ol) |
| M9 | (7-((4-((4-bromophenyl)sulfonyl)piperazin-1-yl)methyl)quinolin-8-ol) |
| M10 | (7-((4-(p-tolylsulfonyl)piperazin-1-yl)methyl)quinolin-8-ol) |
| M11 | (7-((4-((4-isopropylphenyl)sulfonyl)piperazin-1-yl)methyl)quinolin-8-ol) |
| M12 | (7-((4-((4-tert-butylphenyl)sulfonyl)piperazin-1-yl)methyl)quinolin-8-ol) |
| M13 | (7-((4-((4-hydroxyphenyl)sulfonyl)piperazin-1-yl)methyl)quinolin-8-ol) |
| M15 | (7-((4-([1,1'-biphenyl]-4-ylsulfonyl)piperazin-1-yl)methyl)quinolin-8-ol) |
| OXA-B | (ethyl 2-((4-bromophenyl)amino)-2-oxoacetate) |
| OXA-T | (ethyl 2-oxo-2-((3,4,5-trimethoxyphenyl)amino)acetate) |

TABLE I-continued

Chemical structures of the individual compounds of the compound library used for screening

| Cp | Structure |
|---|---|
| OX A-O | (4-methoxyphenyl)-NH-C(O)-C(O)-O-ethyl |
| OX A-2 | phenyl-NH-C(O)-C(O)-NH-CH2-(4-aminophenyl) |
| OX A-3 | (4-chlorophenyl)-NH-C(O)-C(O)-NH-CH2-(4-aminophenyl) |
| OX A-5 | (4-chlorobenzyl)-NH-C(O)-C(O)-NH-CH2-(4-aminophenyl) |
| OX A-4 | (4-methoxybenzyl)-NH-C(O)-C(O)-NH-CH2-(4-aminophenyl) |
| PY-1 | 3-(4-nitrophenyl)-5-phenyl-1H-pyrazole |
| PY-2 | 3-(4-nitrophenyl)-5-(2-methoxyphenyl)-1H-pyrazole |
| 4f | 1-(4-nitrobenzyl)-2-phenyl-1H-indazol-3(2H)-one |
| 4g | 1-benzyl-2-(pyridin-4-yl)-1H-indazol-3(2H)-one |
| 4i | 1-benzyl-2-(4-methoxyphenyl)-1H-indazol-3(2H)-one |
| 4k | 1-benzyl-2-(4-chlorophenyl)-1H-indazol-3(2H)-one |
| SC-4m-9 | 2-[(E)-2-(4-dimethylaminophenyl)vinyl]-4H-chromen-4-one |
| SC-4m-10 | 2-[(E)-2-(4-bromophenyl)vinyl]-4H-chromen-4-one |

TABLE I-continued
Chemical structures of the individual compounds of the compound library used for screening
| Cp | Structure |
|---|---|
| SC-4m-11 | 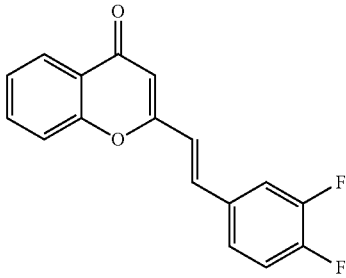 [SMILES: O=c1cc(/C=C/c2ccc(F)c(F)c2)oc2ccccc12] |
| SC-4m-12 | 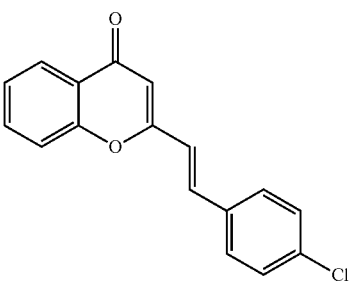 [SMILES: O=c1cc(/C=C/c2ccc(Cl)cc2)oc2ccccc12] |
| SC-4m-13 | 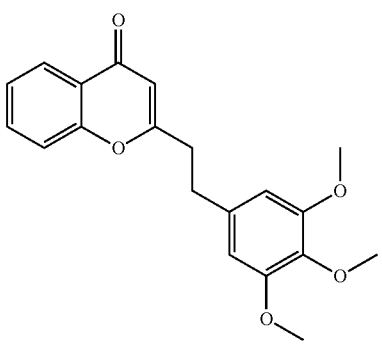 [SMILES: COc1cc(CCc2cc(=O)c3ccccc3o2)cc(OC)c1OC] |
| SC-4m-14 | 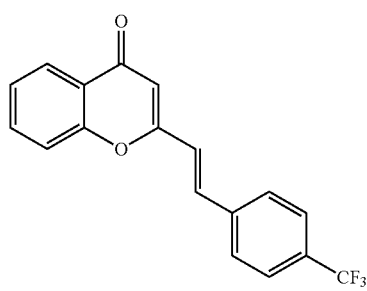 [SMILES: O=c1cc(/C=C/c2ccc(C(F)(F)F)cc2)oc2ccccc12] |
| SC-4m-15 | 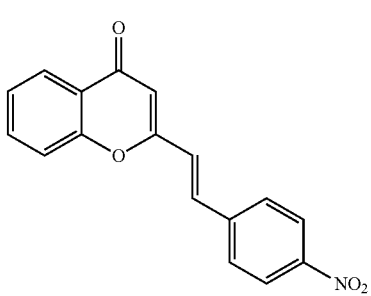 [SMILES: O=c1cc(/C=C/c2ccc([N+](=O)[O-])cc2)oc2ccccc12] |
TABLE I-continued
Chemical structures of the individual compounds of the compound library used for screening
| Cp | Structure |
|---|---|
| SC-4g | 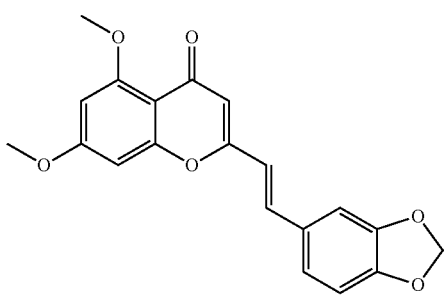 [SMILES: COc1cc(OC)c2c(=O)cc(/C=C/c3ccc4c(c3)OCO4)oc2c1] |
| SC-4h | 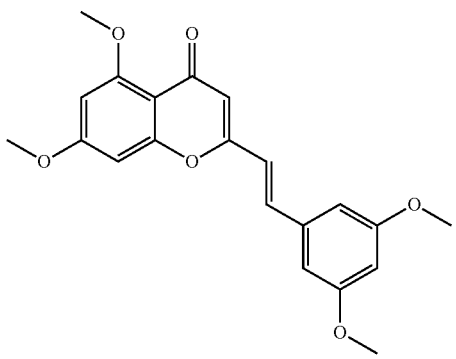 |
| SC-4i | 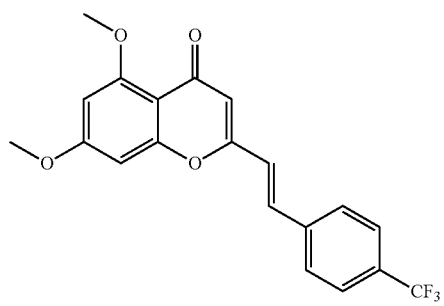 [SMILES: COc1cc(OC)c2c(=O)cc(/C=C/c3ccc(C(F)(F)F)cc3)oc2c1] |
| SC-4j | 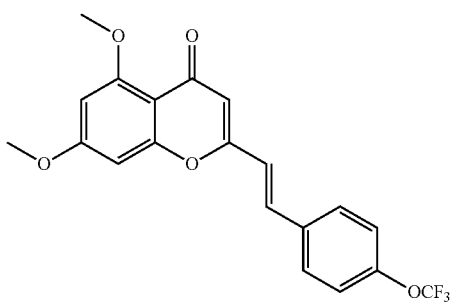 [SMILES: COc1cc(OC)c2c(=O)cc(/C=C/c3ccc(OC(F)(F)F)cc3)oc2c1] |

TABLE I-continued
Chemical structures of the individual compounds of the compound library used for screening
| Cp | Structure |
|---|---|
| SC-4k | 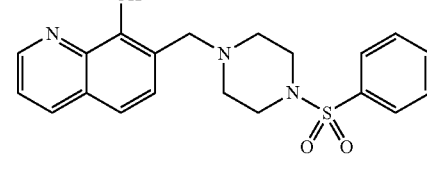 |
| SC-4l | 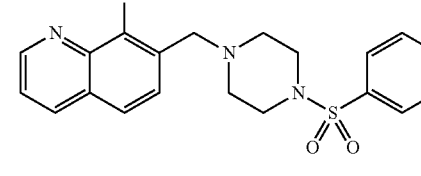 |
| SC-4m | 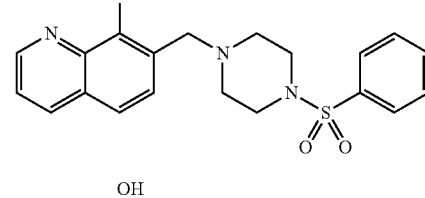 |
| SC-4n | 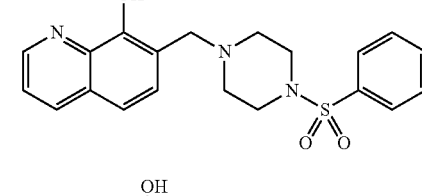 |
| M16 | 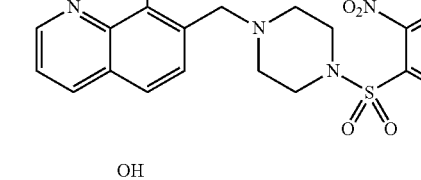 |
| M17 | 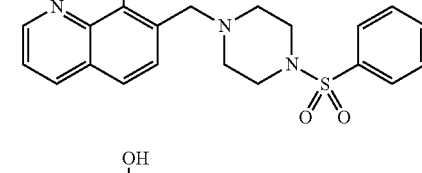 |
| M18 | 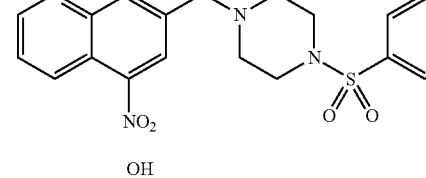 |
| M19 | 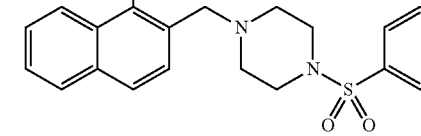 |
| M22 | 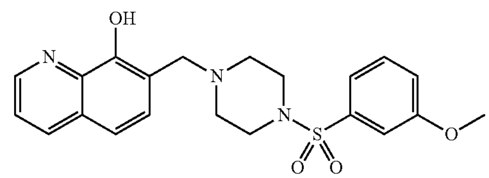 [SMILES: COc1cccc(S(=O)(=O)N2CCN(Cc3ccc4cccnc4c3O)CC2)c1] |
| M24 | 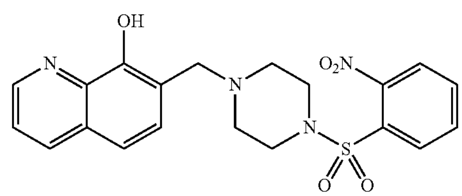 [SMILES: O=[N+]([O-])c1ccccc1S(=O)(=O)N1CCN(Cc2ccc3cccnc3c2O)CC1] |
| M25 | 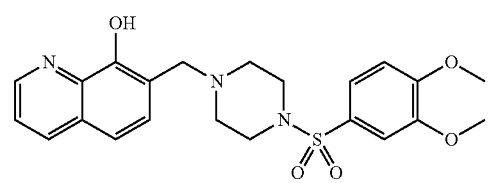 [SMILES: COc1ccc(S(=O)(=O)N2CCN(Cc3ccc4cccnc4c3O)CC2)cc1OC] |
| M26 | 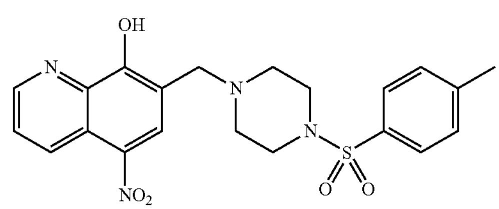 [SMILES: Cc1ccc(S(=O)(=O)N2CCN(Cc3cc([N+](=O)[O-])c4cccnc4c3O)CC2)cc1] |
| M28 | 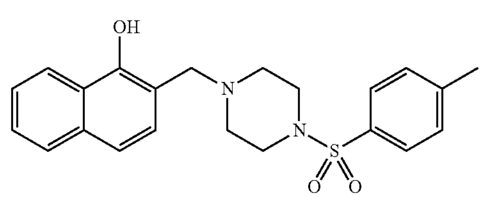 [SMILES: Cc1ccc(S(=O)(=O)N2CCN(Cc3ccc4ccccc4c3O)CC2)cc1] |

TABLE I-continued

Chemical structures of the individual compounds of the compound library used for screening

| Cp | Structure |
|---|---|
| M29 | (1-hydroxynaphthalen-2-yl)methyl-piperazine-N-(4-nitrophenyl)sulfonyl |
| M32 | 8-hydroxyquinolin-7-yl-CH2-NH-CH2CH2-NH-SO2-phenyl |
| M33 | 8-hydroxyquinolin-7-yl-CH2-piperazine-N-benzyl |
| PY-4 | 3-(4-nitrophenyl)-5-(3-methoxyphenyl)-1H-pyrazole |
| PY-5 | 3-(4-nitrophenyl)-5-(3,4-dimethoxyphenyl)-1H-pyrazole |
| PY-7 | 3-(4-nitrophenyl)-5-(4-chlorophenyl)-1H-pyrazole |
| PY-11 | 3-(4-methoxyphenyl)-5-(4-fluorophenyl)-1H-pyrazole |
| PY-13 | 3-(4-methoxyphenyl)-5-(4-aminophenyl)-1H-pyrazole |
| PY-14 | 3-(4-methoxyphenyl)-5-(4-trifluoromethylphenyl)-1H-pyrazole |
| PY-15 | 3-(4-methoxyphenyl)-5-(biphenyl-2-yl)-1H-pyrazole |
| PY-16 | 3-(3-nitrophenyl)-5-phenyl-1H-pyrazole |
| PY-17 | 3-(4-trifluoromethylphenyl)-5-(4-hydroxyphenyl)-1H-pyrazole |
| 4n | 1-benzyl-2-(4-nitrophenyl)-1H-indazol-3(2H)-one |
| 4o | 1-benzyl-2-(3,4,5-trimethoxyphenyl)-1H-indazol-3(2H)-one |
| 3i | 2-azido-N-(4-chlorophenyl)benzamide |

TABLE I-continued
Chemical structures of the individual compounds of the compound library used for screening
| Cp | Structure |
|---|---|
| 3a | 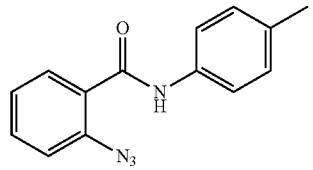 [SMILES: Cc1ccc(NC(=O)c2ccccc2N=[N+]=[N-])cc1] |
| SC-4m-16 | 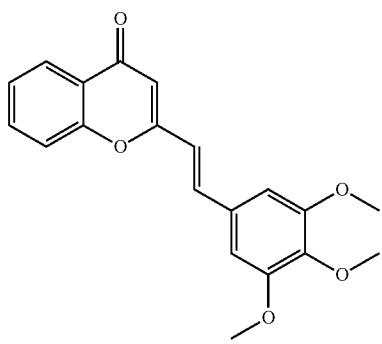 [SMILES: COc1cc(/C=C/c2cc(=O)c3ccccc3o2)cc(OC)c1OC] |
| BA O-1 | 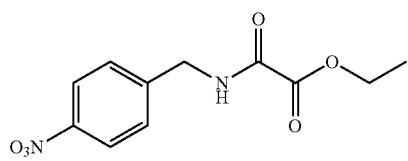 |
| BA O-2 | 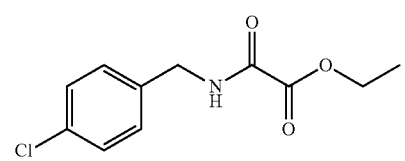 [SMILES: CCOC(=O)C(=O)NCc1ccc(Cl)cc1] |
| PMK-1 | 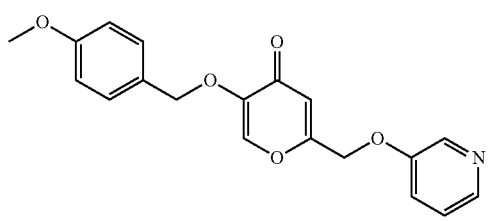 [SMILES: COc1ccc(COc2coc(COc3cccnc3)cc2=O)cc1] |
| PMK-2 | 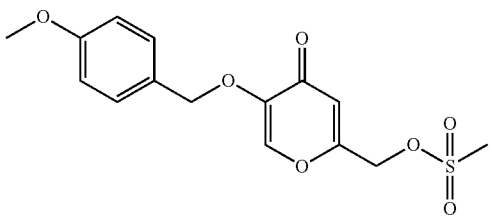 |
| PMK-3 | 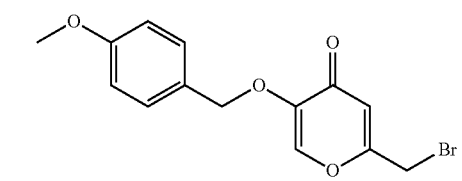 [SMILES: COc1ccc(COc2coc(CBr)cc2=O)cc1] |
TABLE I-continued
Chemical structures of the individual compounds of the compound library used for screening
| Cp | Structure |
|---|---|
| BNO-1 | 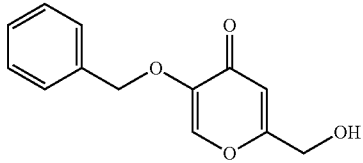 [SMILES: O=c1cc(CO)occ1OCc1ccccc1] |
| SC-4o | 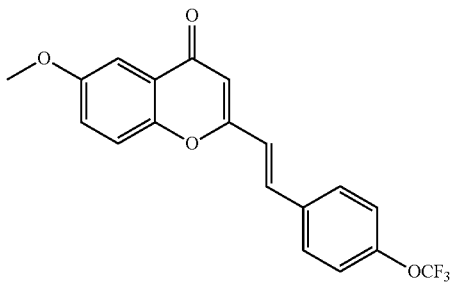 [SMILES: COc1ccc2oc(/C=C/c3ccc(OC(F)(F)F)cc3)cc(=O)c2c1] |
| SC-4p | 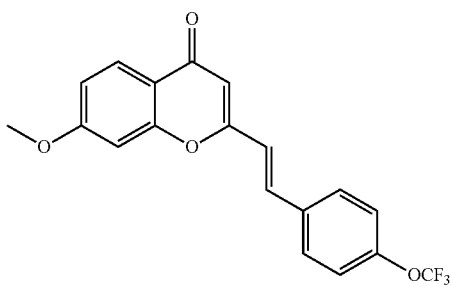 [SMILES: COc1ccc2c(=O)cc(/C=C/c3ccc(OC(F)(F)F)cc3)oc2c1] |
| SC-4a-2 | 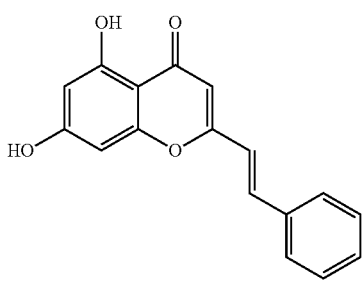 [SMILES: O=c1cc(/C=C/c2ccccc2)oc2cc(O)cc(O)c12] |
| SC-4f-2 | 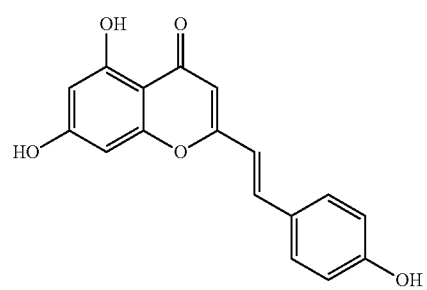 [SMILES: O=c1cc(/C=C/c2ccc(O)cc2)oc2cc(O)cc(O)c12] |

TABLE I-continued
Chemical structures of the individual compounds of the compound library used for screening
| Cp | Structure |
|---|---|
| SC-4j-2 | 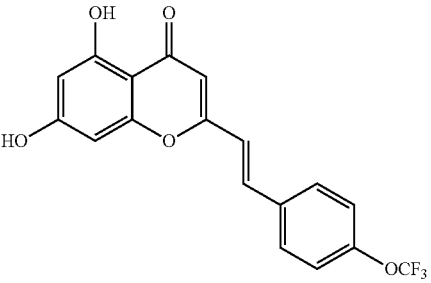 [SMILES: O=c1cc(/C=C/c2ccc(OC(F)(F)F)cc2)oc2cc(O)cc(O)c12] |
| CI-1-1 | 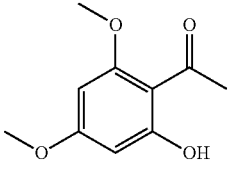 |
| CI-1-2 | 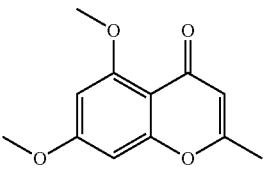 |
| CI-1-3 | 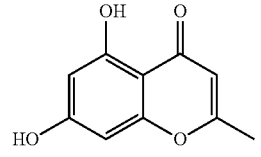 |
| M34 | 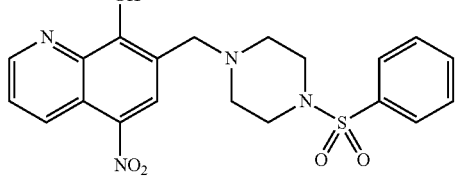 |
| M35 | 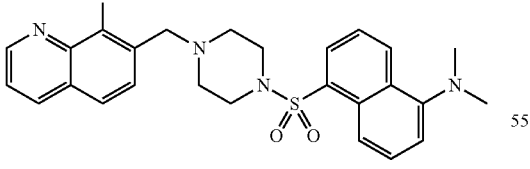 |
| Q1 | 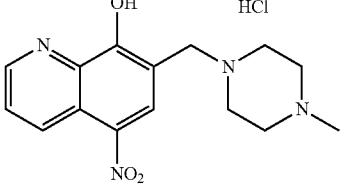 |
| Q2 | 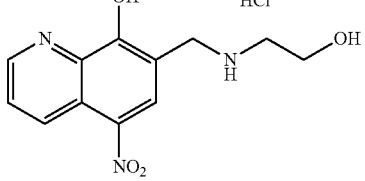 |
| T-1 | 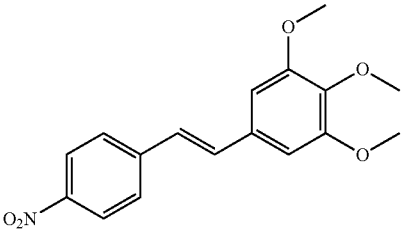 [SMILES: COc1cc(/C=C/c2ccc([N+](=O)[O-])cc2)cc(OC)c1OC] |
| IM6 | 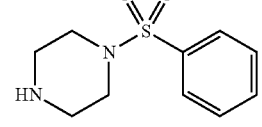 |
| IM7 | 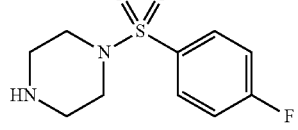 |
| IM8 | 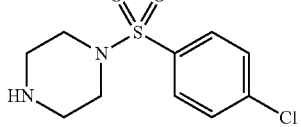 |
| IM9 | 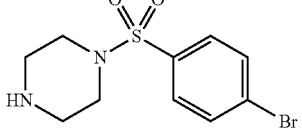 |
| IM11 | 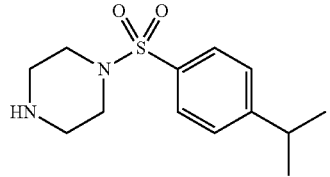 [SMILES: CC(C)c1ccc(S(=O)(=O)N2CCNCC2)cc1] |
| IM12 | 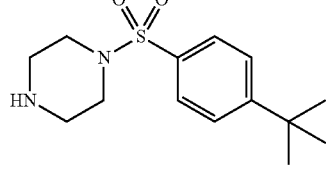 |

TABLE I-continued

Chemical structures of the individual compounds of the compound library used for screening

| Cp | Structure |
|---|---|
| IM14 | piperazine-N-SO2-C6H4-NO2 |
| IM-1 | 4,5-bis-aryl imidazole (4-nitrophenyl, 4-methoxyphenyl) |
| IM-2 | 4,5-bis-aryl imidazole (4-nitrophenyl, 4-chlorophenyl) |
| OXZ-1 | 2,5-bis-aryl oxazole (4-nitrophenyl, 4-methoxyphenyl) |
| OXZ-2 | 2,5-bis-aryl oxazole (4-nitrophenyl, phenyl) |
| OXZ-3 | 5-(4-nitrophenyl)oxazole-2-carboxylic acid ethyl ester |
| SC-4h-2 | 5,7-dihydroxy-2-[(E)-2-(3,5-dihydroxyphenyl)vinyl]-4H-chromen-4-one |
| QN-1 | 8-methoxy-5-nitroquinoline |
| QN-2 | 8-methoxyquinolin-5-amine |
| QN-3 | 8-methoxy-N,N-dimethylquinolin-5-amine |
| 3b | 2-azido-N-(4-methoxyphenyl)benzamide |
| 3c | 2-azido-N-(3,4,5-trimethoxyphenyl)benzamide |
| 3d | 2-azido-N-(4-dimethylaminophenyl)benzamide |
| 3e | 2-azido-N-(pyridin-4-yl)benzamide |
| BNO-2 | 5-(benzyloxy)-4-oxo-4H-pyran-2-carbaldehyde |

TABLE I-continued
Chemical structures of the individual compounds of the compound library used for screening
| Cp | Structure |
|---|---|
| KOJ-1 | 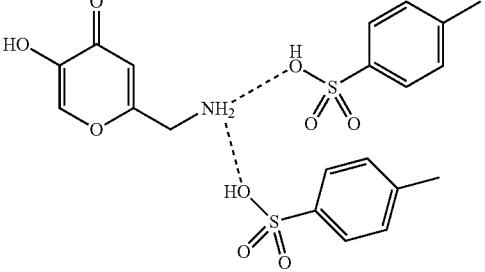 |
| KOJ-2 | 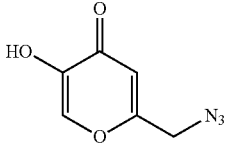 [SMILES: [N-]=[N+]=NCc1cc(=O)c(O)co1] |
| KAI-3 | 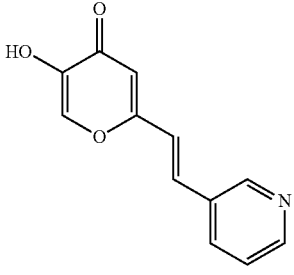 [SMILES: O=c1cc(/C=C/c2cccnc2)occ1O] |
| OBn-KAI-8 | 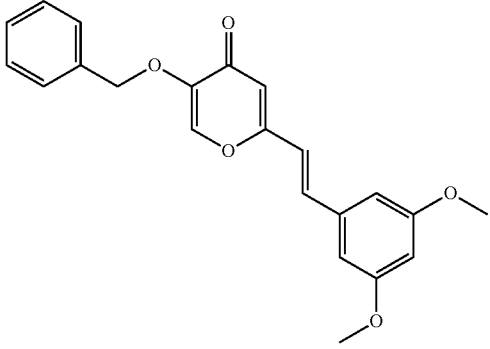 [SMILES: COc1cc(/C=C/c2cc(=O)c(OCc3ccccc3)co2)cc(OC)c1] |
| PMB-KAI-A | 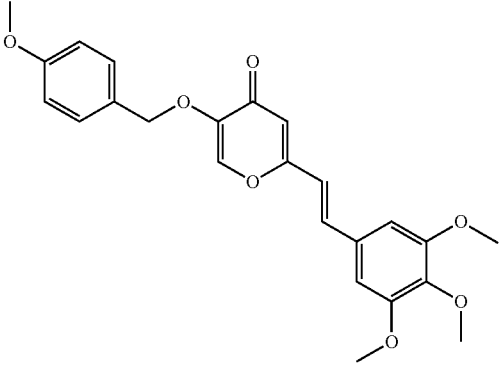 [SMILES: COc1ccc(COc2coc(/C=C/c3cc(OC)c(OC)c(OC)c3)cc2=O)cc1] |
| PMB-KAI-3 | 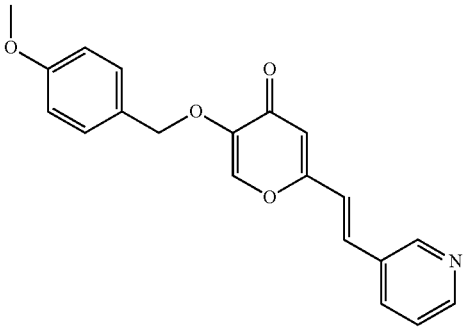 [SMILES: COc1ccc(COc2coc(/C=C/c3cccnc3)cc2=O)cc1] |
| CI-3-2 | 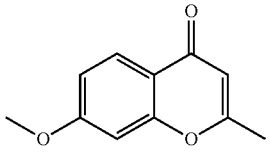 |
| CI-4-1 | 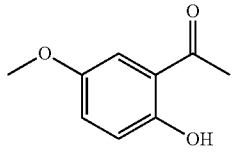 |
| CI-4-2 | 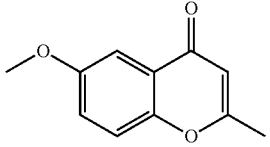 |
| CI-5-1 | 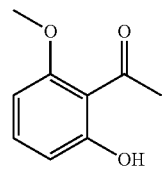 |
| CI-5-2 | 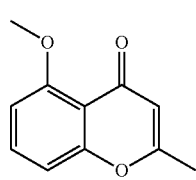 |
| CI-6-1 | 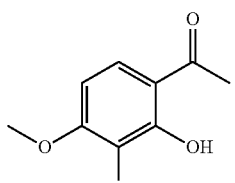 |

TABLE I-continued
Chemical structures of the individual compounds of the compound library used for screening
| Cp | Structure |
|---|---|
| Cl-6-2 | 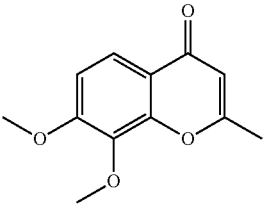 |
| M0 | 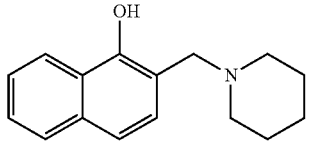 [SMILES: Oc1c(CN2CCCCC2)ccc2ccccc12] |
| IM 15 | 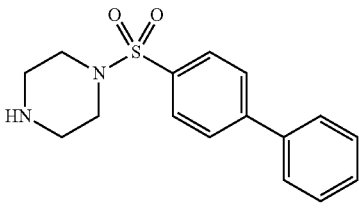 [SMILES: O=S(=O)(c1ccc(-c2ccccc2)cc1)N1CCNCC1] |
| IM 18 | 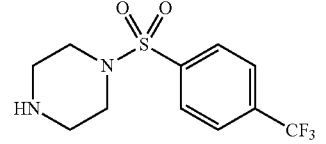 |
| IM 19 | 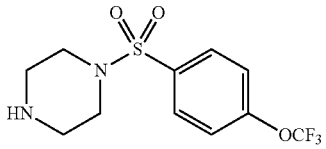 [SMILES: O=S(=O)(c1ccc(OC(F)(F)F)cc1)N1CCNCC1] |
| IM 24 | 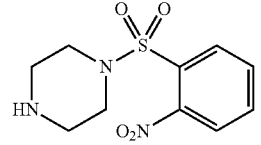 [SMILES: O=[N+]([O-])c1ccccc1S(=O)(=O)N1CCNCC1] |
| IM 25 | 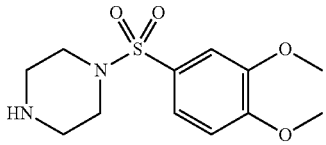 [SMILES: COc1ccc(S(=O)(=O)N2CCNCC2)cc1OC] |
| IM 32 | 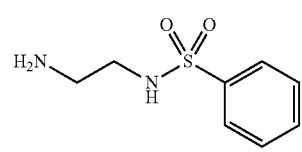 [SMILES: NCCNS(=O)(=O)c1ccccc1] |
| IM 35 | 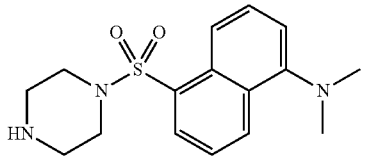 [SMILES: CN(C)c1cccc2c(S(=O)(=O)N3CCNCC3)cccc12] |
| Kia-P-12 | 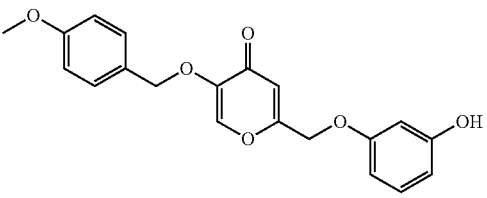 [SMILES: COc1ccc(COc2coc(COc3cccc(O)c3)cc2=O)cc1] |
| Kia-B-12 | 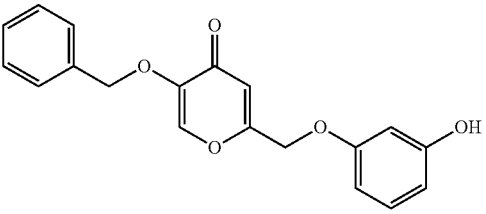 [SMILES: O=c1cc(COc2cccc(O)c2)occ1OCc1ccccc1] |
| Kia-13 | 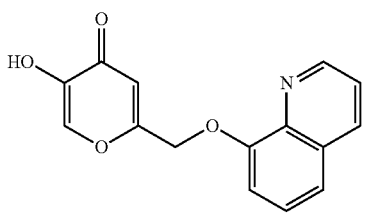 [SMILES: O=c1cc(COc2cccc3cccnc23)occ1O] |
| Kia-B-11 | 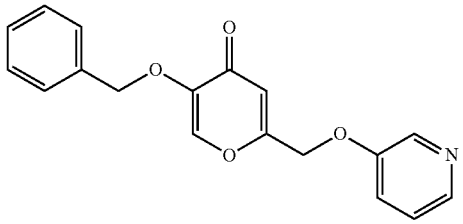 [SMILES: O=c1cc(COc2cccnc2)occ1OCc1ccccc1] |
| OX A-C | 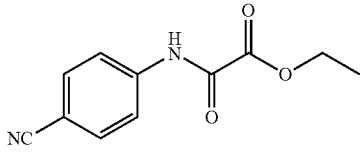 [SMILES: CCOC(=O)C(=O)Nc1ccc(C#N)cc1] |
| QN-5 | 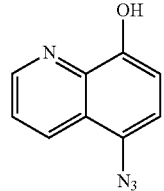 |

TABLE I-continued

Chemical structures of the individual compounds of the compound library used for screening

| Cp | Structure |
|---|---|
| AA-1 | 4-methoxyphenyl-CH(NH$_3^+$Cl$^-$)-COOH |
| AA-2 | 3-methoxyphenyl-CH(NH$_3^+$Cl$^-$)-COOH |
| AA-3 | 3,4-dimethoxyphenyl-CH(NH$_3^+$Cl$^-$)-COOH |
| AA-4 | 4-chlorophenyl-CH(NH$_3^+$Cl$^-$)-COOH |
| AA-5 | 4-(trifluoromethoxy)phenyl-CH(NH$_3^+$Cl$^-$)-COOH |
| 4b | 2-phenyl-1-(4-fluorobenzyl)-1H-indazol-3(2H)-one |
| 4c | 2-phenyl-1-(4-chlorobenzyl)-1H-indazol-3(2H)-one |
| 4d | 2-phenyl-1-(4-bromobenzyl)-1H-indazol-3(2H)-one |
| 3f | 2-azido-N-(4-nitrophenyl)benzamide |
| 3g | 2-azido-N-(4-cyanophenyl)benzamide |
| 3h | 2-azido-N-(4-bromophenyl)benzamide |

Based on this screening platform, 46 derivatives significantly inhibit EGFP expression, of which 36 did not cause apparent cell death. Interestingly, these 36 compounds belonged to three structural series, i.e., IM, CI, and 4x, of which IM25, CI-4-1, and 4e (structures, FIG. 2A) represented the most preferred agents based on high activity and low cytotoxic activity. The dose responses of these agents, along with three structurally related analogues IM9, CI-5-1 and 4o, in suppressing EGFP expression are depicted in FIG. 2B.

These agents vis-à-vis 5-Aza and procainamide were further subjected to ELISA and Western blotting to assess their abilities to suppress EGFP expression as well as MTT assays for their respective cytotoxicity. As revealed in FIG. 3A, only 4e at high concentrations (30 μM) substantially suppressed MCF7 cell viability, while other compounds examined had no apparent effect. Data obtained from ELISA assay support the visualization results in FIG. 2B, in which IM25 exhibits greater demethylation potency than 5-Aza in terms of inhibiting the EGFP expression.

Figure 3:
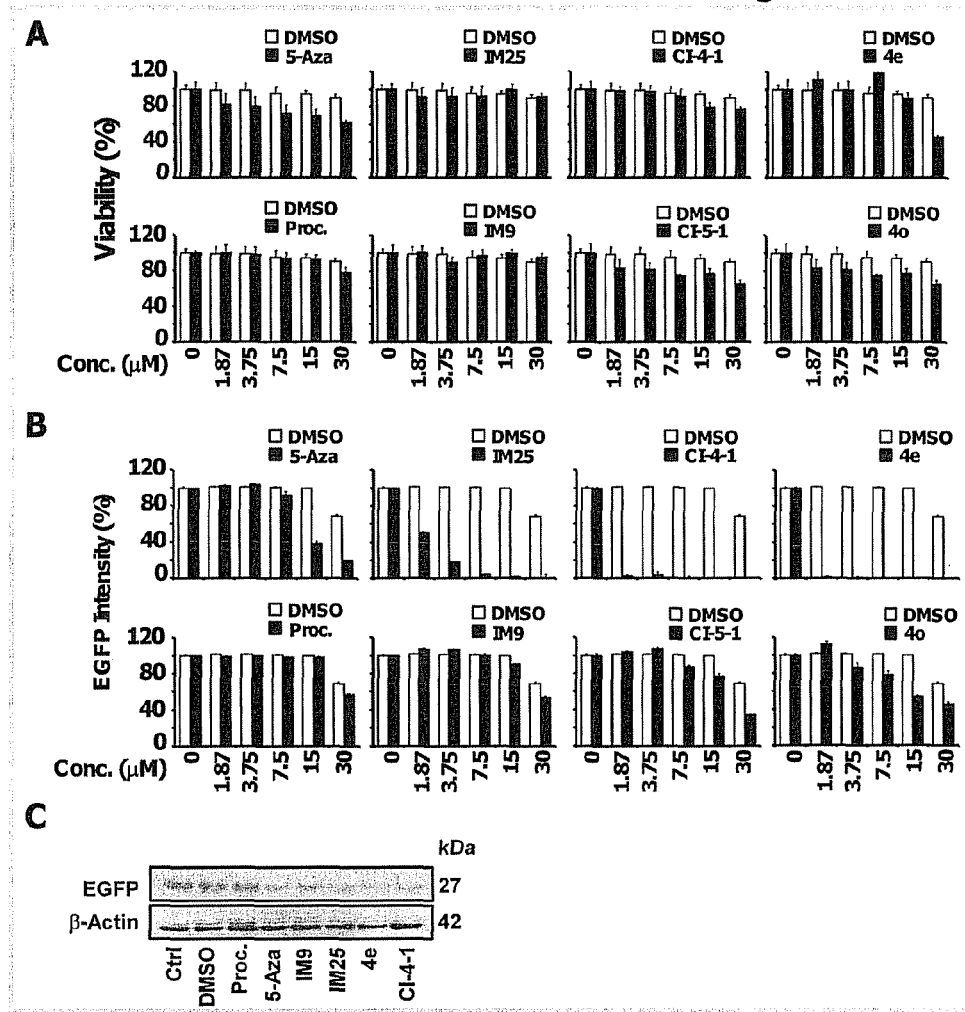
FIG. 3 provides bar graphs and other data illustrating the potency and safety of DNA demethylating agents. Section (A) provides bar graphs comparing the dose-dependent suppressive effects of 5-Aza, procainamide, IM25, and IM9 on the viability of MCF7 cells by MTT assays. Section B) provides bar graphs showing the parallel ELISA analysis of the suppressive effects on EGFP expression in the two-component reporter system. Columns, mean (n=3); error bars, S.D. (C) Western blot analysis of the effects of procainamide, 5-Aza, IM9, and IM25, each at 7.5 µM, on EGFP expression.

In another set of experiment, cells were treated with 7.5 μM of candidate drugs for 5 days, then the cell lysates were harvested and subjected to Western blot. As shown in FIG. 3C, the protein level of EGFP was substantially suppressed by IM25 as well. However, the inventors did notice that the protein level appears to be significantly inhibited by IM9 as well. The inconsistence between the Western blot result versus the ELISA/images is not immediately clear. Results obtained from ELISA and Western blot confirmed that IM25 is an effective demethylation agent in inhibiting EGFP expression.

Figure 4:
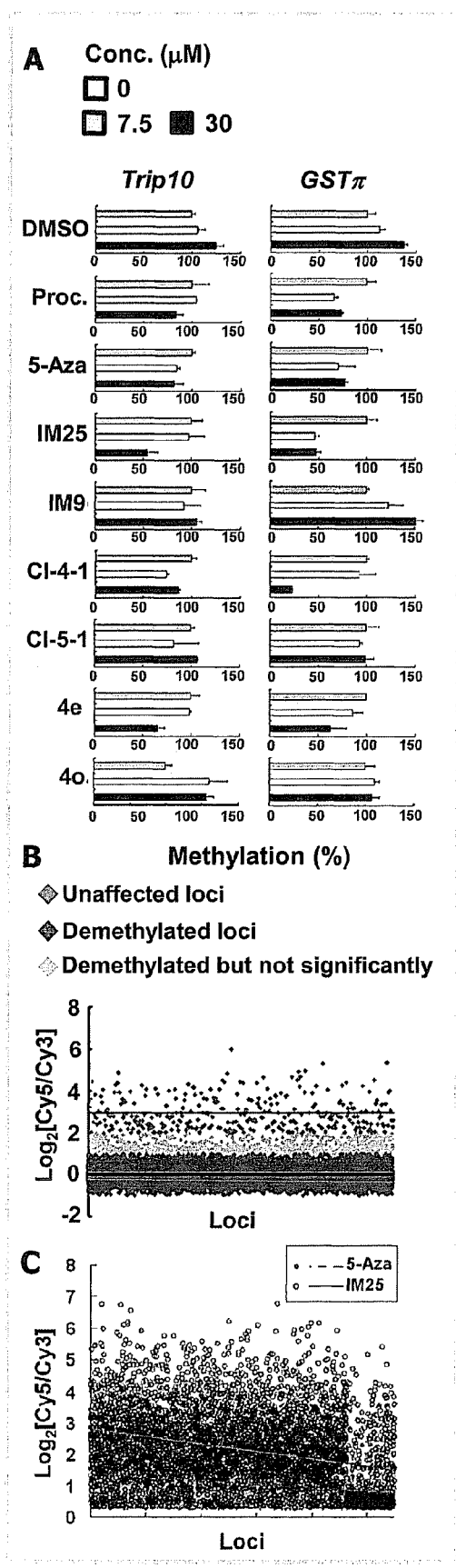
FIG. 4 provides graphs showing drug-induced loci-specific and global demethylation. For section (A), methylation-specific PCR (MSP) was applied to determine the methylation level of Trip10 and GSTp1 in MCF7 cells treated with each of the following derivatives at 7.5 or 30 μM: procainamide, 5-Aza, IM25, IM9, CI-4-1, CI-5-1, 4-e, and 4o, after 5 days of treatment. Procainamide, 5-Aza, IM25, CI-4-1 and 4e significantly reduced the methylation level of GSTp1, while they appear to have weaker effect in demethylating Trip10 promoter (B) DMH analysis of the effect of 7.5 μM IM25 on genome-wide methylation. The higher $Log_2$ [Cy5/Cy3] values indicate stronger demethylation effects. (C) Genome-wide comparison of the demethylation after IM25 and 5-Aza treatment. DMH microarrays identified 5,506 more loci that are demethylated after IM25 treatment (open circles) than the result obtained after 5-Aza treatment (close gray circles). The regressed lines depicted the distribution of demethylation (dashed line for 5-Aza; solid line for IM25) and all the listed 5,506 loci were confirmed significant by ANOVA.

Targeted and global loci demethylation. Both 5-Aza and procainamide have been shown to cause demethylation of GSTp1 (GSTπ1) in colon, prostate, and breast cancer cells. Thus, the inventors conducted MSP to determine the DNA methylation levels of Trip10 and GSTp1 in MCF7 cells treated with IM25, CI-4-1, and 4e vis-à-vis 5-Aza and procainamide. Among these testing compounds, IM25 exhibits the greatest potency in facilitating the demethylation of both Trip10 and GSTp1, CI-4-1 also decreases the methylation level of both genes, but to a lesser extent (FIG. 4A). Compound 4e showed a slight demethylation of GSTp1 only at 30 μM. IM25 was chosen to further elucidate its genome-wide demethylation effects. Cells treated with either IM-25 or DMSO were harvested and subjected to DMH. As demonstrated in FIG. 4B, IM25 was able to cause global demethylation in MCF7 cells. When comparing the global demethylation capacity between IM25 and 5-Aza, 5,506 more demethylated loci out of 244K target loci in Agilent array were identified (FIG. 4C, significant loci confirmed by ANOVA). Therefore, the identified IM25 possesses equal or more demethylation capacity than the known drug.

Discussion

The inventors have demonstrated that a number of procainamide derivatives are effective DNA methylation inhibitors. The methylation inhibitors Azacytidine and 5-Aza have been approved for the treatment of myelodysplastic syndromes by FDA, and they are currently under clinical trials for treatment of solid tumors including breast cancer, lung cancer, and colon cancer, which suggests a similar use for the present compounds. Bender et al., Cancer Res, 58(1), p. 95-101 (1998). Accumulating data also indicate that these demethylation agents could also control stem cell differentiation and treat diseases like sickle cell disease. Despite these promising clinical and in vitro studies for cancer treatment and cell fate manipulation, the side effects such as bone marrow suppression has always been a great concern. The global demethylation analysis by DMH and single target gene validation by MSP indicate that treatment with the compounds of the present invention could disturb MCF7 cell's epigenome. However, many of the compounds of the present invention did not cause overt cell death even at rather high concentrations. The inventors reason that treatment using these compounds may act via altering the gene expression profile and subsequently cause changes in cell physiology/behaviour without affecting cell viability.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A method for treating or preventing cancer in a subject, comprising administering to the subject a pharmaceutical composition including a compound or a pharmaceutically acceptable salt thereof of formula I:

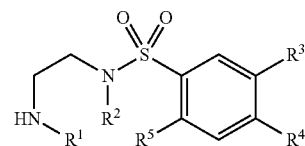

wherein $R^1$ and $R^2$ are either both hydrogen or are linked $CH_2$ moieties forming an unsubstituted ethylene group, and wherein $R^3$, $R^4$, and $R^5$ are independently selected from the group consisting of H, halo, $C_1$-$C_4$ alkyl, $NO_2$, OH, OMe, $CF_3$, and $OCF_3$ moieties.

2. The method of claim 1, wherein $R^1$ and $R^2$ are linked $CH_2$ moieties forming an unsubstituted ethylene group and $R^5$ is H.

3. The method of claim 2, wherein the compound has the structure

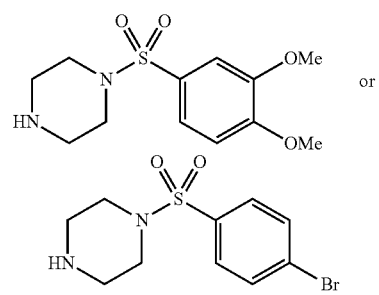

4. The method of claim 2, wherein $R^3$ is H.

5. The method of claim 1, wherein the cancer is breast, prostate, lung, or colon cancer.

6. A method of inhibiting DNA methylation in a cell by contacting the cell with a compound or a pharmaceutically acceptable salt thereof having the structure

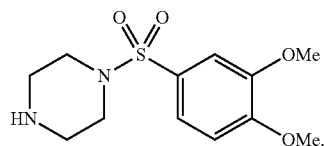 [SMILES: COc1ccc(S(=O)(=O)N2CCNCC2)cc1OC]

* * * * *